United States Patent [19]

Login et al.

[11] Patent Number: 4,732,990

[45] Date of Patent: Mar. 22, 1988

[54] QUATERNIZED NITROGEN CONTAINING COMPOUNDS

[75] Inventors: Robert B. Login, Oakland; Ratan K. Chaudhuri, Butler; David J. Tracy, Lincoln Park; Michael W. Helioff, Westfield, all of N.J.

[73] Assignee: GAF Corporation, Wayne, N.J.

[21] Appl. No.: 922,923

[22] Filed: Oct. 24, 1986

[51] Int. Cl.$^4$ .................. C07D 207/12; C07D 211/76; C07D 295/12
[52] U.S. Cl. .................................... 548/550; 540/451; 540/531; 546/243
[58] Field of Search .................. 548/550; 546/243; 540/451, 531

[56] References Cited

PUBLICATIONS

C. A. 88:169962t, (1978), Surroca et al.
C. A. 82:139964d, (1975), Watanabe et al.
C. A. 92:93862v, (1980), Stephanou et al.

Primary Examiner—Joseph Paul Brust
Attorney, Agent, or Firm—Marilyn J. Maue; Joshua J. Ward

[57] ABSTRACT

The invention relates primarily to quaternized compounds having the formula

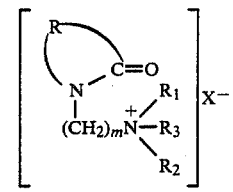

wherein m is an integer having a value of from 1 to 4; R is alkylene having from 3 to 8 carbon atoms and is optionally substituted with $C_1$ to $C_4$ alkyl; $R_1$, $R_2$ and $R_3$ are each independently selected from the group of alkyl, alkyl oxide, alkylhydroxy, alkoxy, aryl, aralkyl, alkaryl, and alkyl amidoalkyl radicals, said groups each having from 1 to 30 carbon atoms and at least one of $R_1$, $R_2$ and $R_3$ is radical having from 8 to 30 carbon atoms; and $X^-$ is a chloride, bromide or iodide anion. The invention also relates to the preparation and use of said quaternized compounds.

9 Claims, No Drawings

QUATERNIZED NITROGEN CONTAINING COMPOUNDS

In one aspect the invention relates to novel quaternized compounds which possess viscosity enhancing and hair conditioning properties, particularly in the presence of anionic surfactants. In another aspect the invention relates to novel quaternized compounds having bactericidal properties. Still another aspect of the invention relates to the preparation of said quaternized compounds and in still another aspect, the invention relates to the use of said compounds in several fields of application.

BACKGROUND OF THE INVENTION

The selection of components for hair and skin treating formulations presents numerous difficulties involving compatibility. Several hair treatment and shampoo formulations have been developed which aim to provide conditioning action during cleansing so as to leave the hair soft, manageable and lustrous and thus to eliminate a separate application of creme rinses or conditioning treatments. Problems arise from the limited compatability of anionic detergents with commercial cationic conditioning agents which precipitate out of solution in shampoo formulations.

Shampoo formulations have employed conventional anionic surfactants such as sodium lauryl sulfate, ammonium lauryl sulfate, amine lauryl sulfates and sodium lauryl sulfate ethers which have been found to be incompatible with most cationic conditioning at effective concentration levels.

Additionally, reproducible thickening for formulations containing anionic detergents such as sodium α-olefin sulfonates is very difficult to achieve.

Still another problem encountered in hair conditioning shampoos is one of a preservative nature. It has been found that shampoos, containing inadequate preservative, on standing develop strands of pseudomonas aerouginosa which are clearly visible in the liquid and which may cause scalp infection. Consequently, separate biocidal agents are added to the formulation to prevent development of this bacteria and prevent skin infection. These and many other problems are encountered in the formulation of various shampoos, conditioners and cream rinses. Certain of these difficulties are also encountered in skin lotions, healing salves, mouthwashes, etc.

Accordingly it is an object of this invention to minimize or obviate the above problems while providing additional benefits in hair and skin treating formulations.

Another object of the invention is to provide novel quaternized nitrogen containing compounds having unique properties.

Another object is to provide novel quaternized nitrogen containing compounds having excellent hair conditioning and thickening properties when incorporated into a shampoo and having high compatibility with components of hair and skin treating formulations.

Another object is to provide an economical and commercially feasible method for the preparation of said novel quaternized nitrogen containing compounds.

Still another object is to provide processes for the use of said quaternized compounds.

These and other objects will become apparent from the following description and disclosure.

THE INVENTION

According to this invention there is provided quaternized compounds having unique properties and defined by the formula

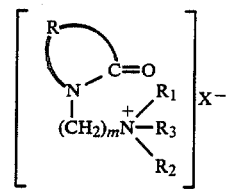

wherein m is an integer having a value of from 1 to 4; R is alkylene having from 3 to 9 carbon atoms and is optionally substituted with $C_1$ to $C_4$ alkyl; $R_1$, $R_2$ and $R_3$ are each independently selected from the group of alkyl, alkyl oxide, alkylhydroxy, alkoxy, aryl, aralkyl, alkaryl and alkyl amidoalkyl radicals, said groups each having from 1 to 30 carbon atoms and at least one of $R_1$, $R_2$ and $R_3$ being a radical having from 8 to 30 carbon atoms; and $X^-$ is a chloride, bromide or iodide anion.

Also included in the scope of this invention are the quaternized compounds of the above general formula wherein $R_2$ and $R_3$ together with the quaternary nitrogen form a 3 to 9 membered ring, said ring containing from 1 to 2 hetero atoms selected from the group of nitrogen and oxygen and said ring being saturated or unsaturated as may occur in the rings of pyrrolidine, morpholine, pyrrole, pyrroline, oxazole, isoxazole, pyrazole, imidazole, pyridine, picoline and diazine. In compounds of this type, $R_1$ may be any of the $R_1$ groups defined above containing from 1 to 30 carbon atoms.

Preferred compounds within the above group are those wherein m is 1; R is $—CH_2—CH_2—CH_2—$; at least one of $R_1$, $R_2$ and $R_3$ is methyl and $X^-$ is a chloride anion. The most preferred compounds of this group are those wherein at least one of $R_2$ and $R_3$ is alkyl containing from 8 to 22 carbon atoms. Examples of compounds within this preferred group include:

N,N-dimethyl-N-nonyl-N-[(2-pyrrolidonyl)methyl]ammonium chloride
N,N-dimethyl-N-decyl-N-[(2-pyrrolidonyl)methyl]ammonium chloride
N,N-dimethyl-N-dodecyl-N-[(2-pyrrolidonyl)methyl]ammonium chloride
N,N-dimethyl-N-tetradecyl-N-[(2-pyrrolidonyl)methyl]ammonium chloride
N,N-dimethyl-N-hexadecyl-N-[(2-pyrrolidonyl)methyl]ammonium chloride
N,N-dimethyl-N-octadecyl-N-[(2-pyrrolidonyl)methyl]ammonium chloride
N,N-dimethyl-N-eicosyl-N-[(2-pyrrolidonyl)methyl]ammonium chloride
N,N-dimethyl-N-docosyl-N-[(2-pyrrolidonyl)methyl]ammonium chloride
N-methyl-N,N-didecyl-N-[(2-pyrrolidonyl)methyl]ammonium chloride
N-methyl-N,N-didodecyl-N-[(2-pyrrolidonyl)methyl]ammonium chloride
N-methyl-N,N-ditetradecyl-N-[(2-pyrrolidonyl)methyl]ammonium chloride
N-methyl-N,N-dihexadecyl-N-[(2-pyrrolidonyl)methyl]ammonium chloride
N-methyl-N,N-dioctadecyl-N-[(2-pyrrolidonyl)methyl]ammonium chloride N-methyl-N,N-dieicosyl-N-[(2-pyrrolidonyl)methyl-]ammonium chloride and
N-methyl-N,N-didocosyl-N-[(2-pyrrolidonyl)methyl-]ammonium chloride However, it is to be understood that other halide salts and that the following quaternary compounds represent examples also within the scope of this invention.

N-methyl-N-ethyl-N-dodecyl-N-[(2-pyrrolidonyl)ethyl]ammonium salt

N-ethyl-N-hexadecyl-N-octadecyl-N-[(2-pyrrolidonyl)methyl]ammonium salt

N,N-dimethyl-N-phenyl-N-[(2-pyrrolidonyl)methyl-]ammonium salt

N,N-dimethyl-N-benzyl-N-[(2-pyrrolidonyl)methyl-]ammonium salt

N-methyl-pyridinyl-N-[(2-pyrrolidonyl)methyl]ammonium salt

N-ethyl-pyrrolidinyl-N-[(2-pyrrolidonyl)methyl]ammonium salt

N-butyl-pyrrolinyl-N-[(2-pyrrolidonyl)methyl]ammonium salt

N-methyl-isoxazolyl-N-[(2-pyrrolidonyl)methyl]ammonium salt

N-methyl-imidazolyl-N-[(2-pyrrolidonyl)methyl]ammonium salt

N-dimethyl-N,N-ditolyl-N-[(2-pyrrolidonyl)methyl-]ammonium salt

N,N-dimethyl-N-triacontyl-N-[(2-pyrrolidonyl)methyl-]ammonium salt

N,N-dimethyl-N-octadecylamidopropyl-N-[(2-pyrrolidonyl)methyl]ammonium salt

N,N-didecyl-N-hexadecyl-N-[(2-pyrrolidonyl)methyl-]ammonium salt

N,N,N-trioctadecyl-N-[(2-pyrrolidonyl)methyl]ammonium salt

N,N-dimethyl-N-octadecyl-N-[(4-methyl-2-pyrrolidonyl)methyl]ammonium salt

N-methyl-N,N-dihexadecyl-N-[(4-butyl-2-pyrrolidonyl)methyl]ammonium salt

N,N-dimethyl-N-hexadecyl-N-[(2-piperidinonyl)methyl]ammonium salt

N-methyl-N,N-dioctadecyl-N-[(2-capronyl)methyl]ammonium salt

N-methyl-N,N-ditetradecyl-N-[(2-azacinonyl)methyl-]ammonium salt

N-methyl-N,N-didodecyl-N-[(2-azacyclononanonyl)-methyl]ammonium salt and others, and the N-methyl-2-capronyl- and $R_1$, $R_2$ and/or $R_3$ amido substituted counterparts of the above listed compounds.

The present quaternary compounds possess unique properties, among which is their ability to build viscosity, while simultaneously providing a hair and skin conditioning capability in cosmetic formulations containing anionic surfactants. These compounds are highly compatible with α-olefin sulfonates and anionic surfactant salts conventionally employed in shampoos and skin lotions. Their compatibility is such that up to 5% by weight or more of the quaternized compounds can be incorporated in the formulation, a characteristic which permits the formation of effective formulations as liquids or gels. In contrast, most prior quaternary viscosity building conditioning compounds are incorporatable only up to 0.5 or 1 wt. percent based on total anionic formulations. The pyrrolidonyl compounds which contain an octadecyl substituent on the quaternary nitrogen are particularly outstanding for their compatability, viscosity building and conditioning properties. The pyrrolidonyl products having a hexadecyl substituent on the terminal amino nitrogen are outstanding for their biocidal properties and can be used in a mouthwash or as a highly compatable preservative in shampoo, hair creams and hand or body lotions. It is contemplated that mixtures of the pyrrolidonyl compound, such as the $C_{16}$ and $C_{18}$ alkyl terminally substituted compounds, can be employed in shampoos, hair conditioners and lotions as an agent which incorporates thickening, conditioning and preservative qualities in one additive; thus eliminating the need for separate chemical components to accomplish these individual needs. These mixtures may also be used to control dandruff or bacterial infections of the scalp and body skin. Generally, the quaternary compounds of this invention are mixed with a standard formulation of shampoo, cream rinse, hand or body lotion or creams, mouthwash, etc., in an effective amount which ranges from between about 0.05 to about 8% by weight, preferably between about 0.5 and about 5% by weight, of the total formulation. The present compounds are also compatible with anionic α-olefin sulfonate which property is surprising since most anionic compounds cause precipitation of cationic agents. However, the present compounds in concentrations up to 5% by weight show no tendency to precipitate after extended periods including periods up to 6 months or more.

The quaternary pyrrolidonyl compounds of this invention are prepared by an economically feasible process which involves the reaction between a tertiary amine and a N-haloalkyl lactam having a 5 to 10 membered ring. A general equation for the preparation is defined by the equation:

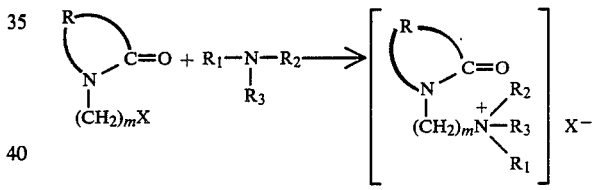

wherein m, R, $R_1$, $R_2$, $R_3$ and X- are as defined above and X is chloro, bromo or iodo.

Examples of suitable lactam reactants include the N-chloromethyl, N-bromomethyl and N-iodomethyl derivatives of 2-pyrrolidone, 4-methyl-2-pyrrolidone, 4-butyl-2-pyrrolidone, 2-piperidinone, 2-piperidone, methyl-2-piperidinone, 2-caproyl, hexahydro-2-(1H)-azacinone, octahydro-2H-azaonin-2-one, octahydro-2-(1H)-azecinone and $C_1$ to $C_4$ alkyl substituted derivatives located on an alkylene group in the heterocyclic ring of these lactams. Mixtures of these lactam reactants can also be employed to provide a correspondingly mixed quaternary product, if desired. Of these lactam reactants the N-halomethyl-2-pyrrolidones and N-halomethyl caprolactams are preferred and the N-chloromethyl lactams are most preferred.

Preferred tertiary amines employed in the present process include reactive methyl and ethyl tertiary amines having one or two $C_8$ to $C_{22}$ alkyl groups, for example N-methyl-N,N-didecyl amine, N,N-dimethyl-N-octadecyl amine, N,N-dimethyl-N-dodecyl amine, N,N-dimethyl-N-hexadecyl amine, N,N-dimethyl-N-eicosyl amine, and N-ethyl-N,N-dihexadecyl amine. However, also included in the scope of this invention are reactive amines wherein a $C_8$ to $C_{30}$ alkyl group is itself substituted with alkoxy of 1 to 4 carbon atoms, phenyl, benzyl, amido, can be employed, as well as tertiary amines having 1 to 3 aryl groups, eg. phenyl, benzyl, tolyl, xylyl, etc., such as triphenyl amine, dimethyl tolyl amine, ethyl di(phenyl) amine, methyl di(nonylphenyl) amine, dimethyl, chlorophenyl amine and other halo substituted phenyl amines. Tri-$C_8$ to $C_{22}$ alkyl amines can also be employed in the reaction, examples of which include trihexadecyl amine, trioctadecyl amine, tridodecyl amine, tridecyl amine, etc. Also included are heterocyclic tertiary amines such as morpholine, imidazoline, piperazine, pyridine etc.

The most preferred amine reactants of this invention are those defined by the formula

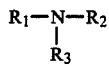

wherein $R_1$ is methyl, $R_2$ is methyl or $C_8$ to $C_{22}$ alkyl and $R_3$ is $C_8$ to $C_{22}$ alkyl.

The process is effected by reacting the tertiary amine and the haloalkyl lactam at a temperature between about 25° and about 150° C., preferably between about 60° and about 100° C., under a pressure of from about 0 to about 50 psig, preferably atmospheric pressure, for a period up to about 10 hours, usually not more than 5 hours is required to complete the reaction. From the above equation, it is seen that stoichiometric amounts of haloalkyl lactam and amine are used in the reaction. However, an excess of one or the other of the components is practicible in the process. Generally, for economic considerations, a mole ratio of between 1:1.5 and about 1.5:1 is employed; although, a slight excess of the tertiary amine to insure complete reaction of the lactam is recommended. Accordingly, the most preferred mole ratio of lactam to amine is about 1:1.01-1:1.03.

It is also recommended that the haloalkyl lactam be added gradually or dropwise to the amine at the beginning of the ensuing exothermic reaction. At the completion of the reaction, a solid product is formed and recovered. Since the reaction is quantitative, the product can be used as is or, when a slight excess of the amine is employed, it can be neutralized with a weak acid such as acetic, lactic or citric acid.

For incorporating into a standard formulation of shampoo, cream rinse, hand or body lotion, etc., the present product is dissolved in an inert solvent such as water, propylene glycol, ethanol, etc., and the solution in the desired amount is mixed into the formulation to provide a homogeneous liquid, gel, cream or lotion. Incorporation of the present product is usually affected at room temperature under atmospheric pressure and requires no special formulating technique. However, for certain formulations incorporation of the present product can be effected at temperatures up to about 85° C. Amphoteric-containing shampoo formulations are best prepared by initially preparing an aqueous solution of the quaternized product and the amphoteric surfactant and then adding the solution to the shampoo formulation.

Having generally described the invention, reference is now had to the accompanying examples which set forth preferred embodiments, but which are not to be construed as limiting to the scope of the invention as more broadly set forth above and in the appended claims.

EXAMPLE I

To a 1 liter, 4-neck flask equipped with mechanical stirrer, reflux condenser, thermometer, and dropping funnel was added N,N-Dimethyl-N-Octadecyl Amine (150.29 g, 0.505 mole) which was heated with stirring to 70° C. under $N_2$ blanket after which the heating source was removed and N-chloromethyl-2-pyrrolidone (66.8 g, 0.5 mole) was added to the amine dropwise over a period of 25 minutes. An exothermic reaction ensued and was controlled at 100° C. by the rate of addition of N-chloromethyl-2-pyrrolidone. The reaction mixture changed from a liquid to a paste during the addition of N-chloromethyl-2-pyrrolidone and finally to a solid (powder) on completion of the reaction. The yield of N,N-dimethyl-N-octadecyl-N-[(2-pyrrolidonyl)methyl]ammonium chloride, m.p. 110°-115° C., was quantitative. The content of the quaternary compound was determined by titration. (Mercuric Acetate method as described by Sidney Siggia, "Quantitative Organic Analysis via Functional Group", 1963, 3d Ed., John Wiley & Sons, pages 552-554).

EXAMPLE II

The reaction of Example I was repeated except that the amine used was N,N-dimethyl-N-hexadecyl amine (2% molar excess with respect to N-chloromethyl-2-pyrrolidone). The product, N,N-dimethyl-N-hexadecyl-N-[(2-pyrrolidonyl)methyl]ammonium chloride, m.p. 98°-102° C., was neutralized with acetic acid and recovered in quantitative yield.

EXAMPLE III

The reaction of Example II was repeated except that the amine used was N,N-dimethyl-N-tetradecyl amine. The corresponding N,N-dimethyl-N-tetradecyl-N-[(2-pyrrolidinyl)methyl]ammonium chloride, m.p. 94°-97° C., was recovered in quantitative yield.

EXAMPLE IV

The reaction of Example II was repeated except that the amine used was N,N-dimethyl-N-dodecyl amine. The corresponding N,N-dimethyl-N-dodecyl-N-[(2-pyrrolidonyl)methyl]ammonium chloride, m.p. 99°-103° C., was recovered in quantitative yield.

EXAMPLE V

The reaction of Example II was repeated except that the amine used was N,N-dimethyl-N-decyl amine. The corresponding N,N-dimethyl-N-decyl-N-[(2-pyrrolidonyl)methyl]ammonium chloride, m.p. 101°-105° C., was recovered in quantitative yield.

EXAMPLE VI

The reaction of Example II was repeated except that the amine used was N,N-dimethyl-N-octyl amine. The corresponding N,N-dimethyl-N-octyl-N-[(2-pyrrolidonyl)methyl]ammonium chloride, m.p. 93°-97° C., was recovered in quantitative yield.

EXAMPLE VII

The reaction of Example II was repeated except that the amine used was N,N-dioctadecyl-N-methyl amine. The corresponding N-methyl-N,N-dioctadecyl-N-[(2-pyrrolidonyl)methyl]ammonium chloride, m.p. 54°-58° C., was recovered in quantitative yield.

EXAMPLE VIII

The reaction of Example II was repeated except that the amine used was N,N-didecyl-N-methyl amine. The product, N-methyl-N,N-didecyl-N-[(2-pyrrolidonyl)-methyl]ammonium chloride, was obtained as a paste.

Analyses of the products prepared in Examples I–VIII are reported in following Table I.

TABLE I
ANALYSIS OF TERTIARY AMINE/N—CHLORO-METHYLPYRROLIDONE (CMP) COMPOUNDS

| Tertiary Amine | Equivalents | ANALYSIS* % Quat. | % Free Amine** |
|---|---|---|---|
| $CH_3(CH_2)_7N(CH_3)_2$ | 1.02 | 97.2 | 0.8 |
| $CH_3(CH_2)_9N(CH_3)_2$ | 1.02 | 97.9 | 2.3 |
| $CH_3(CH_2)_{11}N(CH_3)_2$ | 1.02 | 96.8 | 1.6 |
| $CH_3(CH_2)_{13}N(CH_3)_2$ | 1.02 | 94.5 | 2.5 |
| $CH_3(CH_2)_{15}N(CH_3)_2$ | 1.02 | 98.0 | 1.4 |
| $CH_3(CH_2)_{17}N(CH_3)_2$ | 1.02 | 97.0 | 3.9 |
| $[CH_3(CH_2)_9]_2NCH_3$ | 1.02 | 95.2 | 2.9 |
| $[CH_3(CH_2)_{17}]_2NCH_3$ | 1.02 | 96.1 | 4.5 |

*% quat. and free amine determined by Mercuric Acetate Method
**The free amine titer can be adjusted by the addition of slightly more CMP during preparation.

EXAMPLE IX

The reaction of Example II is repeated except that the lactam used is N-bromomethyl-2-caprolactam, the N,N-dimethyl-N-hexadecyl-N-[(2-capronyl)methyl]ammonium bromide is recovered as a solid product.

Other products described herein are prepared by the general procedure outlined above with the substitution of the desired 2-pyrrolidonyl-, 2-piperidinonyl-, 2-capronyl-, 2-azacycloctanone-, 2-azacyclononanone-, 2-azacyclodecanone- or 2-piperidinone-lactam reactant and/or the substitution of the desired tertiary amine.

EXAMPLE X

Quaternized compounds of the present invention have shown disinfectant properties. The following describes experiments employed to ascertain the disinfectant effect of certain species of the present quaternized compounds against two common bacteria, namely, staphylococcus, aurus and Pseudomonas aeruginosa.

An AOAC use dilution study* was conducted on 8 of the products listed in Table II. More specifically, stainless steel cylinders of 10 mm length and 6 mm inner diameter were immersed in a synthetic broth containing subculture fluid, thioglycollate media USP, for 10 minutes at 20° C. after which the contents were dried. The cylinders were then immersed in an aqueous solution of the test product for 10 minutes at 20° C. For testing efficacy against staphlococcus aureus, 400 ppm of product in solution was used. For testing efficacy against pseudomonas aeruginosa, 800 ppm of product in solution was employed. The results of these primary tests were recorded and the above procedure was repeated for secondary testing, the results of which were also recorded. Each test was made in 30 replicates and the results reported in Table II show the number of individual cultures in the primary and in the secondary testing where bacterial growth was not arrested.

*"Official Methods of Analysis of the Association of Official Analytical Chemists", 13th Ed., 1980, Chapter 4, para. 4.007–4.011.

TABLE II

Compound Tested $$\left[ \begin{array}{c} \text{pyrrolidone ring with } N-CH_2-\overset{+}{N}(R_1)(R_2)(R_3) \end{array} \right] Cl^-$$

| $R_1$ | $R_2$ | $R_3$ | Staphlococcus aureus (400 ppm of test compd.) Growth: primary/secondary | Pseudomonas aeruginosa (800 ppm of test compd.) Growth: primary/secondary |
|---|---|---|---|---|
| $CH_3$ | $CH_3$ | $C_8H_{17}$ | 30/30* | 30/30* |
| $CH_3$ | $CH_3$ | $C_{10}H_{21}$ | 30/30* | 0/8 |
| $CH_3$ | $C_{10}H_{21}$ | $C_{10}H_{21}$ | 0/2 | 1/5 |
| $CH_3$ | $CH_3$ | $C_{12}H_{25}$ | 1/3 | 1/1 |
| $CH_3$ | $CH_3$ | $C_{14}H_{29}$ | 1/8 | 2/19 |
| $CH_3$ | $CH_3$ | $C_{16}H_{33}$ | 0/0** | 0/1 |
| $CH_3$ | $CH_3$ | $C_{18}H_{37}$ | 1/7 | 8/24 |
| $CH_3$ | $C_{18}H_{37}$ | $C_{18}H_{37}$ | 30/30* | 30/30* |

*bacteria growth in all 30 tests
**no bacteria growth in any of the 30 tests

In the 2-pyrrolidonyl series, it appears that the N,N-dimethyl-N-octadecyl-N-[(2-pyrrolidonyl)methyl]ammonium chloride, the N,N-dimethyl-N-hexadecyl-N-[(2-pyrrolidonyl)methyl]ammonium chloride, the N,N-dimethyl-N-dodecyl-N-[(2-pyrrolidonyl)methyl]ammonium chloride and the N-methyl-N,N-didecyl-N-[(2-pyrrolidonyl)methyl]ammonium chloride products are outstanding in their control of staphylococcus aureus and pseudomonas aeruginosa.

Although all of the present quaternized compounds possess excellent surfactant properties, certain members are particularly recommended for incorporation into specific types of cosmetic formulations. Table III lists some of such uses for individual quaternized products within the scope of this invention, together with a brief description of the benefits derived from their incorporation.

Generally, the present products are added to the formulations in amounts between about 0.1 and about 5 wt. %, based on active ingredients. The quaternized compounds in Table III have the general formula:

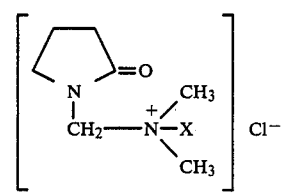

except No. 15 which has the formula:

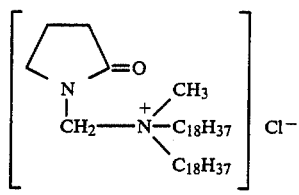

TABLE III

| No. | Compd where X is | For Formulation In | Benefits Achieved |
|---|---|---|---|
| 1 | n-octadecyl | cream rinse | improved wet/dry combing improved luster & shine |
| 2 | n-octadecyl | hair conditioner | improved wet/dry combing overall conditioning & improved luster & shine |
| 3 | n-hexadecyl | blow-dry styling lotion | protection from heat, improved luster, shine, body & overall conditioning, preservation and styling |
| 4 | n-octadecyl | moisturizing lotion | facilitates rub-in, smoother feel & high compatability with other components |
| 5 | n-octadecyl | bubble bath | high compatability, smooth after-feel & viscosity enhancement |
| 6 | n-hexadecyl | mouthwash | good germidical properties clean, pleasant taste |
| 7 | n-octadecyl | syndet bar | high compatability & improved feel |
| 8 | n-octadecyl | after-sun lotion | high compatability, smoother feel & facilitates rub-in |
| 9 | n-octadecyl | non-alcoholic mousse | conditioning, improved body, luster & shine, softer feel |
| 10 | n-octadecyl | self-heating aerosol shave cream | high compatability, smoother skin feel, thermal stability & improved spreadability |
| 11 | n-octadecyl | mousse hand & body lotion | improved rub-in and smoother after-feel |
| PRESENT COMPOUNDS USED IN MIXTURES FOR INCORPORATION | | | |
| 12 | compd. where X is n-octadecyl + compd where X is n-hexadecyl combined in n-dodecyl-2-pyrrolidone | conditioning shampoo | combined overall conditioning and cleaning, compatability with anionic components, improved wet/dry combing, luster & shine, viscosity enhancement & extra body |
| 13 | compd. where X is n-octadecyl in n-dodecyl-2-pyrrolidone | oily hair shampoo | "greaseless" conditioning, viscosity enhancement & improved wet/dry combability, shine & luster |
| 14 | compd. where X is n-octadecyl + compd where X is n-hexadecyl | hair mist conditioner | improved wet/dry combability, luster & shine, preservation and conditioning |
| | | hot oil treatment | improved conditioning, luster, shine, wet/dry combability, hair body & preservation |
| | | after shave balm | improved rub-in, skin conditioning & preservation and smoother skin feel |
| 15 | n-dioctadecyl | conditioning hair spray | dry compatability, improved luster, shine |

TABLE III-continued

| No. | Compd where X is | For Formulation In | Benefits Achieved |
|---|---|---|---|
| | | | and manageability. |

Examples of specific formulations for the above uses achieving the benefits noted are presented as follows.

| Ingredients | Parts by Weight |
|---|---|
| CREAM RINSE | |
| Compound No. 1 in Table III | 2.0 |
| cetyl alcohol | 2.0 |
| emulsifying wax | 2.0 |
| citric acid to pH | 4 |
| deionized water | qs |
| fragrance | qs |
| preservative | qs |
| HAIR CONDITIONER | |
| Compound No. 2 in Table III | 4.0 |
| PEG-8 Distearate | 2.5 |
| mineral oil | 1.5 |
| lanolin alcohol | 1.0 |
| stearic acid | 1.0 |
| PPG-20 methyl glucose ether | 1.0 |
| hydrolized animal protein | 0.25 |
| citric acid to pH | 4 |
| deionized water | qs |
| preservative | qs |
| fragrance | qs |
| BLOW DRY STYLING LOTION | |
| Compound No. 3 in Table IIII | 1.5 |
| ethanol | 3.0 |
| polyquaternium* 11 | 2.0 |
| PEG-10 Castor oil | 0.2 |
| fragrance | 0.2 |
| phosphoric acid to pH | 6 |
| deionized water | qs |
| CONDITIONING HAIR SPRAY | |
| Compound No. 15 in Table III | 2.0 |
| ethanol | 75.51 |
| ethyl ester of PVM/MA** copolymer | 4.0 |
| 2-amino-2-methyl-1-propanol 99% | 0.09 |
| fragrance | 0.2 |
| propellant | 20.0 |

*the quaternized ammonium polymer formed by reacting dimethyl sulfate and a copolymer of vinyl pyrrolidone and dimethylamino methylacrylate
**vinyl methyl ether/maleic anhydride

| Ingredients | Parts by Weight |
|---|---|
| CONDITIONING SHAMPOO | |
| Compound mixture of No. 12 in Table III | |
| X is n-hexadecyl | 1.5 |
| x is n-octadecyl | 1.5 |
| dodecylpyrrolidone | 0.6 |
| polyquaternium 11 | 0.5 |
| sodium laureth-4-phosphate | 0.8 |
| ammonium lauryl sulfate | 40.0 |
| silk protein | 0.25 |
| tetrasodium ethylenediamine tetra-acetic acid | 0.2 |
| deionized water | qs |
| colorant | qs |
| fragrance | qs |
| MOISTURIZING LOTION | |
| Compound No. 4 in Table III | 2.0 |
| mineral oil 70 CTS | 2.0 |
| stearic acid | 3.0 |
| emulsifying wax | 3.0 |
| Dimethicone* 200 CTS | 1.5 |
| Carbomer 934** | 0.15 |
| Oleth-20*** | 1.0 |
| triethanolamine 98% | 1.0 |
| deionized water | qs |
| preservative | qs |
| fragrance | qs |

*a mixture of methylated siloxane polymers end-blocked with trimethyl siloxy units (dimethylpolysiloxane)
**cross-linked polymer of acrylic acid
***PEG ether of oleyl alcohol

| Ingredients | Parts by Weight |
|---|---|
| BUBBLE BATH | |
| Compound No. 5 in Table III | 3.0 |
| ammonium nonoynol-4-sulfate | 30.0 |
| sodium cocoyl isothionate | 10.0 |
| cocamidopropyl hydroxysultaine | 10.0 |
| cocamide diethanolamide | 6.0 |
| sodium methyl cocyl taurate | 20.0 |
| aloe vera gel | 1.0 |
| coconut oil | 1.0 |
| glycol stearate | 1.0 |
| deionized water | qs |
| preservative | qs |
| colorant | qs |
| SHAMPOO FOR OILY HAIR | |
| Compound No. 13 in Table III | 3.0 |
| n-dodecylpyrrolidone | 1.0 |
| tetrasodium ethylenediamine tetra-acetic acid | 0.2 |
| sodium lauryl sulfate | 20.0 |
| alpha-olefin sulfonate | 20.0 |
| polyquaternium 11 | 0.5 |
| deionized water | qs |
| preservative | qs |
| colorant | qs |
| fragrance | qs |
| added inorganic salts as desired for viscosity modification | |
| MOUTHWASH | |
| Compound No. 6 in Table III | 0.05 |
| alcohol, 190° | 20.00 |
| thymol | 0.03 |
| glycerine | 10.00 |
| flavor | 2.0 |
| distilled water | qs |
| polysorbate 80 | 2.00 |
| SYNDET BAR (Superfatted) | |
| Compound No. 7 in Table III | 0.5 |
| stearic acid, triple pressed | 32.00 |
| kettle soap | 9.80 |
| sodiumcocoyl isethionate | 49.00 |
| sodium methyl cocoyl taurate | 6.90 |
| citric acid, 50% aqueous | 0.60 |
| titanium dioxide | 0.20 |
| fragrance | 1.00 |
| WATER RESISTANT EMOLLIENT AFTER SUN LOTION | |
| Compound No. 8 in Table III | 3.0 |
| mink Oil, Light Fraction | 11.00 |
| glyceryl stearate, self emulsifying | 1.00 |
| stearic acid | 2.50 |
| mineral oil and lanolin alcohol | 2.00 |
| myristyl myristate | 3.000 |
| mineral oil | 10.00 |
| PVP/Eicosene copolymer | 2.00 |
| triethanolamine | 0.70 |
| sorbitol | 3.00 |
| hydroxyethylcellulose | 0.30 |
| distilled water | qs |
| preservative | qs |
| fragrance | qs |
| NON-ALCOHOLIC CONDITIONING MOUSSE | |
| Compound No. 9 in Table III | 5.00 |
| PVP K-30 | 2.00 |
| Oleth-20 | 0.50 |
| fragrance | qs |
| deionized water | 77.50 |
| propellant A-46 | 15.00 |
| SELF-HEATING AEROSOL SHAVING CREAM | |
| (Used dual dispensing valve containing 30 ml stearic acid and 11% hydrogen peroxide) | |
| Compound No. 10 in Table III | 2.00 |
| stripped coconut fatty acid | 1.10 |
| sorbitol | 10.00 |
| stearic acid | 4.20 |
| PEG-40 soritan peroleate | 2.00 |
| triethanolamine | 3.00 |
| potassium hydroxide | 1.00 |
| potassium sulfite | 9.00 |
| fragrance | 0.80 |
| butyrated hydroxy toluene (BHT) | 0.01 |
| butyrated hydroxy anisole (BHA) | 0.01 |
| deionized water | qs |
| HAIR MIST CONDITIONER (w/o added preservative) | |
| 50/50 Mixture No. 14 in Table III | 1.00 |
| propylene glycol dicaprylate/dicaprate copolymer | 0.30 |
| oleamidopropyl dimethylamine | 0.50 |
| deionized water | 98.2 |
| CATIONIC MOUSSE HAND/BODY LOTION | |
| (Used 85 Parts of the following formula to 15 parts propellant A-46) | |
| Compound No. 11 in Table III | 0.50 |
| acetylated polyoxyethylene lanolin | 2.00 |
| ethoxylated lanolin alcohols | 1.00 |
| glyceryl stearate, self-emulsifying | 5.50 |
| cetyl alcohol | 1.50 |
| mineral oil, 70 CTS | 1.50 |
| stearyl alcohol | 1.50 |
| glycerin | 3.00 |
| isopropyl myristate | 4.00 |
| dimethicone, 100 CTS | 2.00 |
| water | qs |
| preservative | qs |
| fragrance | qs |
| HOT OIL TREATMENT (w/o added preservative) | |
| 50/50 mixture No. 14 in Table III | 1.50 |
| oleamidopropyl dimethyl amine | 1.00 |
| polyethylene glycol 6000 distearate | 2.00 |
| hexylene glycol | 4.00 |
| lactic acid, 88% to pH | 4.4 |
| color | qs |
| deionized water | qs |
| AFTER SHAVE BALM | |
| 50/50 mixture No. 14 in Table III | 1.00 |
| Carbomer 941 | 0.20 |
| tetrasodium ethylene diamine tetra-acetic acid | 0.10 |
| cetearyl alcohol* and polyethylene glycol ether of cetearyl alcohol | 2.50 |
| isopropyl myristate | 1.00 |
| Oleth-20 | 1.00 |
| methyl gluceth 20 | 2.00 |
| triethanolamine, 98% | 0.20 |
| propylene glycol | 3.00 |
| SDA denatured alcohol | 7.50 |
| PVP/dimethylaminoethyl methacrylate | 7.00 |
| fragrance | 1.00 |
| distilled water | qs |

*50/50 mixture of cetyl and stearyl alcohols

The above examples are representative or preferred embodiments of the present invention; however, it will be understood that other species of instant quaternized lactams can be substituted in the above formulations to provide the benefits indicated. Also, in the preparation of the quaternized lactams described in Examples I–IX, other lactam and/or tertiary amine reactants described herein can be substituted to provide the corresponding quaternized products which are also included within the scope of this invention. Particularly recommended among these substituted species are the halomethyl-2-caprolactam reactants and the amidoalkyl-substituted or hydroxy-substituted tertiary amine reactants which also provide useful bactericidal and viscosity enhancing properties.

What is claimed is:

1. The quaternized compound having the formula

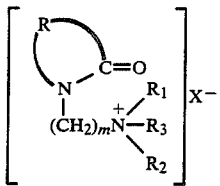

wherein $X^-$ is a chloride, bromide or iodide anion; m is an integer having a value of from 1 to 4; R is $C_3$ to $C_9$ alkylene and is optionally substituted with $C_1$ to $C_4$ alkyl and $R_1$, $R_2$ and $R_3$ are each independently selected from the group consisting of alkyl, hydroxyalkyl, aryl, alkaryl, and aralkyl radicals, said groups having from 1 to 30 carbon atoms and at least one of $R_1$, $R_2$ and $R_3$ having at least 8 carbon atoms in a linear chain.

2. The quaternized compound of claim 1 wherein m has a value of 1; R taken together with —CO and —N— forms a pyrrolidonyl or a caprolactam ring; $X^-$ is a chloride anion and $R_1$, $R_2$ and $R_3$ are alkyl.

3. The quaternized compound of claim 2 wherein at least one of $R_1$, $R_2$ and $R_3$ is alkyl having from 8 to 22 carbon atoms and another of $R_1$, $R_2$ and $R_3$ is methyl.

4. The quaternized compound of claim 3 which is the N,N-dimethyl-N-octadecyl-N-[(2-pyrrolidonyl)methyl]ammonium salt.

5. The quaternized compound of claim 3 which is the N-methyl-N,N-dioctadecyl-N-[(2-pyrrolidonyl)methyl]ammonium salt.

6. The quaternized compound of claim 3 which is the N,N-dimethyl-N-hexadecyl-N-[(2-pyrrolidonyl)methyl]ammonium salt.

7. The quaternized compound of claim 3 which is the N,N-dimethyl-N-decyl-N-[(2-pyrrolidonyl)methyl]ammonium salt.

8. The quaternized compound of claim 3 which is the N-methyl-N,N-didecyl-N-[(2-pyrrolidonyl)methyl]ammonium salt.

9. The quaternized compound of claim 3 which is the N,N-dimethyl-N-dodecyl-N-[(2-pyrrolidonyl)methyl]ammonium salt.

* * * * *